United States Patent [19]
Gaskin

[11] Patent Number: 5,804,976
[45] Date of Patent: Sep. 8, 1998

[54] DEVICE FOR DETERMINING THE RATIO OF SUBSTANCES

[75] Inventor: Graham James Gaskin, Aberdeen, United Kingdom

[73] Assignee: Macaulay Land Use Research Institute of Craigiebuckler, Aberdeen, United Kingdom

[21] Appl. No.: 706,675

[22] Filed: Sep. 6, 1996

[51] Int. Cl.[6] ........................... G01N 22/04; G01R 27/06
[52] U.S. Cl. ................... 324/645; 324/637; 324/643; 324/72.5
[58] Field of Search ................... 324/637, 640, 324/642, 643, 647, 694, 696, 704, 705, 713, 715, 717, 72.5

[56] References Cited

U.S. PATENT DOCUMENTS

| | | | |
|---|---|---|---|
| 3,079,551 | 2/1963 | Walker | 324/643 |
| 3,710,244 | 1/1973 | Rauchwerger | 324/664 |
| 3,870,951 | 3/1975 | Brown et al. | 324/689 |
| 4,546,645 | 10/1985 | Delmulle et al. | 324/690 X |
| 4,996,490 | 2/1991 | Scott et al. | 324/639 |
| 5,069,070 | 12/1991 | Schmitz | 324/645 X |
| 5,073,756 | 12/1991 | Brandelik | 324/643 |
| 5,083,090 | 1/1992 | Sapsford et al. | 324/632 |
| 5,136,249 | 8/1992 | White et al. | 324/643 |
| 5,256,978 | 10/1993 | Rose | 324/601 |
| 5,397,994 | 3/1995 | Phare | 324/668 |

Primary Examiner—Glenn W. Brown
Attorney, Agent, or Firm—Ratner & Prestia

[57] ABSTRACT

A measurement device and a method for indicating the ratio of two or more substances having different dielectric constants which form a body of material is described. The measurement device comprises an oscillator (1), a transmission line (5) connected at one end to the oscillator (1) and a probe unit (7) connected to the other end of the transmission line (5). The oscillator (1) transmits an oscillating signal via the transmission line (5) to the probe unit (7), where the probe unit (7) contacts with the body of material. The difference in voltage amplitude between two points in the transmission line (5) is measured, and is indicative of the ratio of the two or more substances.

20 Claims, 2 Drawing Sheets

DEVICE FOR DETERMINING THE RATIO OF SUBSTANCES

BACKGROUND OF THE INVENTION

This invention relates to a measurement device preferably, but not exclusively, for the measurement of soil water content.

The measurement of soil water content and soil water fluxes is critical to a wide range of environmental studies including plant water status, climatology, acidification, pollution and nutrient uptake. Applications for a soil water measuring system include irrigation sites to ensure crop yield optimisation, flood control and arable sites to determine timing of fertiliser and effluent inputs.

Traditional non-destructive techniques for the measurement of soil water content include the Neutron Probe technique, Time Domain Reflectometry (TDR) and the use of gypsum moisture blocks. While these methods have proved fairly successful, each has limitations in field applications.

The Neutron Probe which detects water thermalised neutrons from an Americium-Beryllium fast neutron source, has the disadvantage that the system requires the installation of permanent metal access tubes into the soil to permit the probe head to be lowered to the depths where the measurements are to be taken. Also, the application of this technique is precluded at unattended sites since not only is a radioactive source used but operator intervention is necessary.

Gypsum moisture blocks, which are based on the measurement of the electrical resistance between inert metal electrodes cast into blocks of gypsum, are generally unsuitable for longer term monitoring of soil water content due to the acidic nature of some surrounding soils causing dissolution.

T.D.R. is based on the measurement of the dielectric constant of the material under study. T.D.R. systems produce a trace of time against reflection amplitude of a fast rise time electromagnetic pulse which is applied to a transmission line probe formed in the soil. However, inconsistencies around the probe wires can produce anomalies on the trace which obscure the pulse start and end points.

SUMMARY OF THE INVENTION

In accordance with the present invention, a measurement device to indicate the ratio of two or more substances forming a body of material and having different dielectric constants comprises an oscillator, a transmission means connected at one end to the oscillator, and a probe unit connected to the other end of the transmission means, the transmission means transmitting an oscillating signal produced by the oscillator to the probe, the probe unit for contacting the material, and measurement means for measuring the difference in voltage between two spaced apart points on the transmission means, the voltage difference being indicative of the ratio of the two or more substances.

According to another aspect of the invention, there is provided a method of indicating the ratio of two or more substances having different dielectric constants which form a body of material, the method comprising contacting a probe with the material to be measured, generating an oscillatory signal, passing the signal to the probe via a transmission means, and measuring the difference in voltage between two spaced apart points on the transmission means.

Preferably, the said points are the ends of the transmission means.

Preferably, the difference in voltage which is measured is the difference in voltage amplitude.

The invention has the advantage that it uses the effect of a voltage standing wave being set up on the transmission means if the impedance of the probe unit differs from that of the transmission means to permit real time analysis. In particular for a soil moisture measurement device, this also permits the use of far less expensive technology than existing methods, is much simpler to construct and is capable of continuous unattended operation.

Typically, the material is soil, but alternatively may be any composition of non-metallic powdered, liquid or solid substances into which the probe unit may be inserted.

Preferably, the oscillator provides a sinusoidal output and more preferably the frequency of said sinusoidal output is between 30 MHz and 1 GHz. Most preferably the said frequency is 100 MHz.

This has the advantage of minimizing the effects of d.c. conductance through the medium, without incurring high frequency losses.

Preferably the transmission means is a co-axial transmission line, and more preferably is 75Ω co-axial transmission line. Preferably the length of the co-axial transmission line is in the range 400 mm to 520 mm, and most preferably the length of the co-axial transmission line is 500 mm.

Preferably, the apparatus output is a d.c. voltage output and most preferably, but not exclusively, the d.c. voltage output ranges from −1V to +1V.

The invention has the advantage that the d.c. voltage output requires no complex interpretation, and provides a real time measurement system.

Typically, the probe unit has one or more pins which are connected to the outer conductor of the co-axial transmission line and one or more pins coupled to the inner conductor of the co-axial transmission line.

Preferably there are three pins connected to the outer conductor of the co-axial transmission line. Typically there is one pin connected to the inner conductor of the co-axial transmission line.

Typically the three pins connected to the outer conductor of the co-axial transmission line are equispaced around the circumference of the probe unit.

Preferably the pin connected to the inner conductor of the co-axial transmission line projects from the centre of the probe unit.

In one example of the invention the outer pins are longer than the central pin.

Typically the outer pins are 70 mm long and the central pin is 60 mm long.

This has the advantage of reducing radio frequency propagation from the central pin to the atmosphere.

However, alternatively, the outer pins may be of the same length as the central pin.

Typically, the ratio is a volumetric ratio.

Preferably, for a ratio of 1:1 water to soil, the probe impedance will equal 75Ω. Typically for a ratio of greater than 1:1 water to soil, the probe impedance will be less than 75Ω and accordingly for a ratio of less than 1:1 water to soil, typically the probe impedance will be greater than 75Ω.

Alternatively the probe unit may be an open end of the co-axial transmission line.

Typically, the d.c. voltage output is produced by means of an electronic circuit.

Preferably the input to the electronic circuit is the voltage amplitude across the co-axial transmission line.

BRIEF DESCRIPTION OF THE DRAWINGS

An example of a measurement device in accordance with the invention will now be described with reference to the accompanying drawings, in which.

DESCRIPTION OF THE PREFERRED EMBODIMENT

The moisture measurement device is based on the fact that in a water:soil:air matrix, the dielectric constant is dominated by the amount of water present. The dielectric constant of water is approximately equal to eighty whereas the dielectric constant of soil is approximately equal to four and the dielectric constant of air is equal to one. Therefore any changes in the volumetric ratio of water will result in a substantial change in the dielectric constant of the matrix.

Figure 1:
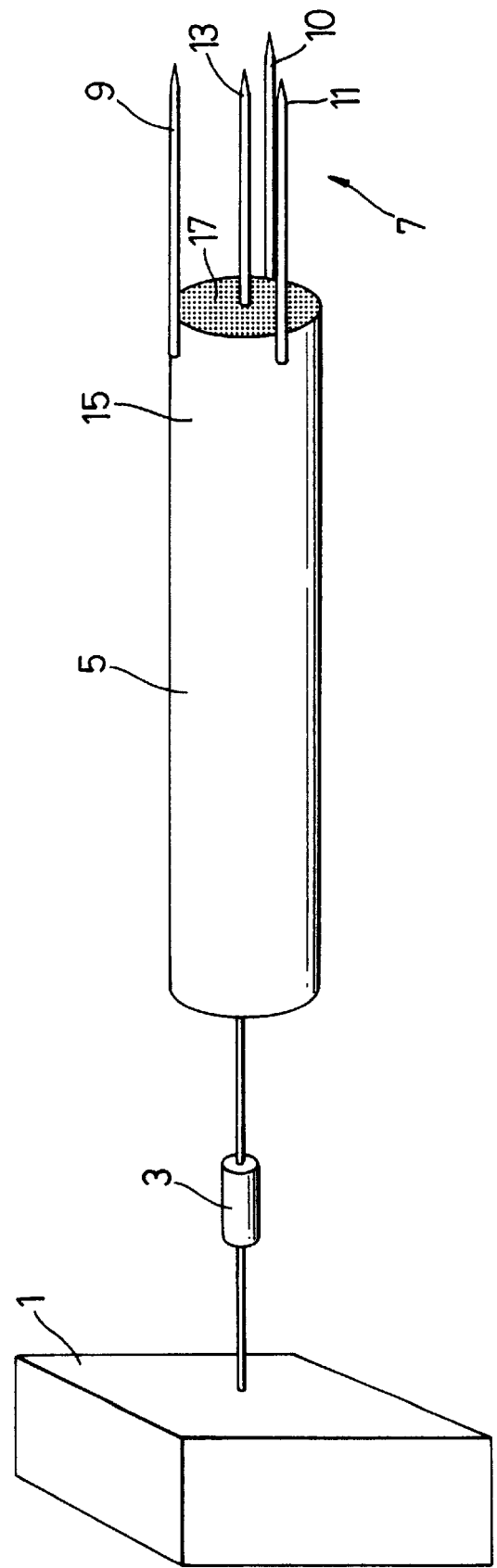
FIG. 1 is a schematic drawing of an apparatus for measuring the water content of soil.

FIG. 1 shows an oscillator 1, connected to resistor 3 which is further connected to one end of a co-axial transmission line 5. The oscillator 1 is of sinusoidal waveform output. The oscillator 1 operates in the frequency range 30 MHz to 1 GHz, where the preferred output frequency is 100 MHz. A sensing probe unit 7 is connected to the other end of the co-axial transmission line 5, and has three outer pins 9, 10, 11 and one inner pin 13. The three outer pins 9, 10, 11 are connected to the outer conductor 15 of the co-axial transmission line 5 and the inner pin 13 is connected to the inner conductor 17 of the co-axial transmission line 5.

The pins 9, 10, 11, 13 mounted on the sensing probe unit 7 are inserted into the medium requiring the water content to be measured.

To reduce radio frequency propagation from the inner pin 13 to the atmosphere when the moisture measurement device is in use, the outer pins 9, 10, 11 are longer than the inner pin 13. The length of the outer pins 9, 10, 11 is approximately 70 mm and the length of the inner pin 13 is approximately 60 mm.

Alternatively, as the radio frequency propagation from the inner pin 13 to the atmosphere may be minimal, the inner 13 and outer pins 9, 10, 11 are all of the same length, to aid construction of the probe unit 7.

The co-axial transmission line 5 is of a fixed impedance, typically 75Ω, and the sensing probe unit 7 has an impedance that is dependent on the dielectric constant of the medium surrounding the inner pin 13 and the outer pins 9, 10, 11.

When the probe unit 7 is inserted in soil with a volumetric ratio of 1:1 water to soil the probe unit impedance will equal 75Ω, that is, the same impedance as the 75Ω co-axial transmission line 5. For a volumetric ratio of greater than 1:1 water to soil the probe unit 7 impedance will be less than 75Ω, and accordingly, for a volumetric ratio of less than 1:1 water to soil the probe unit 7 impedance will be greater than 75Ω.

In an alternative embodiment of the present invention an open-ended (not shown) co-axial transmission line 5 is used without the pins 9, 10, 11, 13 arrangement.

In operation, the signal produced by 100 MHz oscillator 1 is propagated along co-axial transmission line 5 into the sensing probe unit 7. If the impedance of the sensing probe unit 7 differs from that of the co-axial transmission line 5, then a proportion of the incident signal is reflected back towards the 100 MHz oscillator 1. The reflected component interferes with the incident signal, causing a voltage standing wave to be set up on the co-axial transmission line 5. Thus there is a variation of voltage amplitude distributed along the length of the co-axial transmission line 5.

The difference in voltage amplitude at the start and end of the co-axial transmission line 5 can be theoretically derived. The optimum length of the co-axial transmission line 5 can be calculated for use with the 100 MHz oscillator 1, since the velocity of an electromagnetic wave propagating through a transmission line is known. The length of the co-axial transmission line 5 is in the range of 400 mm to 520 mm, and for a 100 MHz oscillator 1 output frequency, the optimum length of the co-axial transmission line 5 is 500 mm.

Alternatively, the difference in voltage amplitude may be measured at two known points along a length of coaxial transmission line, the two known points being 500 mm apart.

Therefore, by measuring the difference in voltage amplitude between known points, such as the two ends of the co-axial transmission line 5, relative impedance of the sensing probe unit 7 can be judged.

Figure 2:
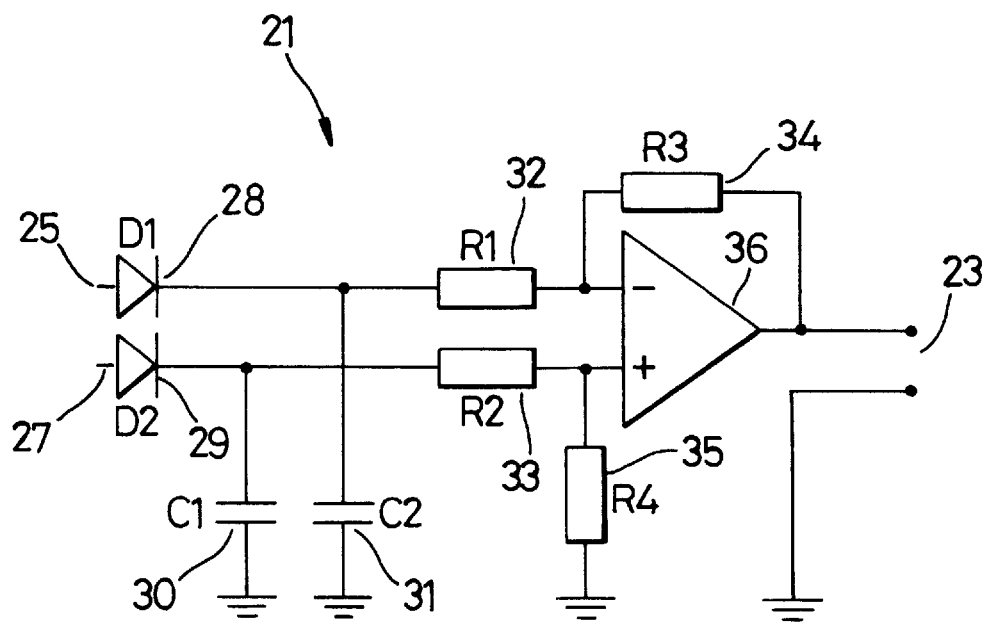
FIG. 2 is a circuit drawing of an impedance sensing device for use with the apparatus of FIG. 1.

With regard to FIG. 2, a circuit 21 is shown whose output 23 is a d.c. voltage representation of the level of moisture being measured.

The first input 25 to the circuit 21 is connected to the end of the co-axial transmission line 5 that is closest to the 100 MHz oscillator 1, and the second input 27 is connected to the other end of the co-axial transmission line 5.

The circuit 21 consists of two rectifying diodes 28, 29, two capacitors 30, 31, four resistors 32, 33, 34, 35 and an operational amplifier 36. With the components connected as shown in FIG. 2, the circuit 21 provides two d.c. voltage signals one of which is subtracted from the other, giving a d.c. voltage output that is representative of the level of moisture being measured. The d.c. voltage output will normally be in the range −1V to +1V.

The system is powered by a 12V battery, but is capable of operation if the supply voltage drops to 7V or rises to 16V.

Improvements and modifications may be incorporated without departing from the scope of the invention.

I claim:

1. A measurement device to indicate the ratio of two or more substances forming a body of material and having different dielectric constants, the device comprising an oscillator, a transmission means connected at one end to the oscillator, and a probe unit for contacting the material, where the probe is connected to the other end of the transmission means, the transmission means transmitting an oscillating signal produced by the oscillator to the probe, and measurement means for measuring the difference in voltage between two spaced apart points on the transmission means, the voltage difference being indicative of the ratio of the two or more substances.

2. A measurement device according to claim 1, wherein the oscillator provides a sinusoidal output.

3. A measurement device according to claim 2, wherein the frequency of said sinusoidal output is between 30 MHz and 1 GHz.

4. A measurement device according to claim 1, in which said points are the ends of the transmission means.

5. A measurement device according to claim 1, wherein the transmission means is a co-axial transmission line.

6. A measurement device according to claim 5, wherein the length of the co-axial transmission line is in the range 400 mm to 520 mm.

7. A measurement device according to claim 5, wherein the probe unit is an open-ended co-axial transmission line.

8. A measurement device according to claim 5, wherein the probe unit has one or more pins which are connected to an outer conductor of the co-axial transmission line and one or more pins coupled to an inner conductor of the co-axial transmission line.

9. A measurement device according to claim 8, wherein there are three pins connected to the outer conductor of the co-axial transmission line and one pin connected to the inner conductor of the co-axial transmission line.

10. A measurement device according to claim 1, further comprising an output which is indicative of the ratio of the two or more substances, where the output is a d.c. voltage output.

11. A measurement device according to claim 10, wherein the d.c. voltage output ranges from −1V to +1V.

12. A measurement device according to claim 10, wherein the d.c. voltage output is produced by means of an electronic circuit.

13. A measurement device according to claim 12, wherein the input to the electronic circuit is the voltage across the co-axial transmission line.

14. A measurement device according to claim 1, wherein the body of material is soil and for a ratio of 1:1 water to soil the probe impedance will equal 75Ω, for a ratio of greater than 1:1 water to soil the probe impedance will be less than 75Ω and for a ratio of less than 1:1 water to soil the probe impedance will be greater than 75Ω.

15. A measurement device according to claim 1, wherein the difference in voltage which is measured is the difference in voltage amplitude.

16. A method of indicating the ratio of two or more substances have different dielectric constants which form a body of material, the method comprising contacting the body of material to be measured with a probe, generating an oscillatory signal, passing the signal to the probe via a transmission means, and measuring the difference in voltage between two spaced apart points on the transmission means, where the difference in voltage is indicative of the ratio of the two or more substances.

17. A method according to claim 16, wherein the difference in voltage which is measured is the difference in voltage amplitude.

18. A method according to claim 16, wherein the oscillator provides a sinusoidal output of between 30 MHz and 1 GHz.

19. A method according to claim 16, wherein said points are the ends of the transmission means.

20. A method according to claim 16, wherein the transmission means is a 75Ω co-axial transmission line.

* * * * *